US008183525B2

(12) United States Patent
Chambers et al.

(10) Patent No.: US 8,183,525 B2
(45) Date of Patent: May 22, 2012

(54) METHOD AND SYSTEM FOR ANALYSING A DOSE FORMULATION OF A METERED DOSE DEVICE

(75) Inventors: Frank Chambers, Loughborough (GB); Andrew Feilden, Loughborough (GB)

(73) Assignee: Astrazeneca AB, Sodertalje (SE)

( * ) Notice: Subject to any disclaimer, the term of this patent is extended or adjusted under 35 U.S.C. 154(b) by 336 days.

(21) Appl. No.: 12/523,293

(22) PCT Filed: Jan. 15, 2008

(86) PCT No.: PCT/SE2008/000027
§ 371 (c)(1),
(2), (4) Date: Jul. 15, 2009

(87) PCT Pub. No.: WO2008/088270
PCT Pub. Date: Jul. 24, 2008

(65) Prior Publication Data
US 2011/0108727 A9     May 12, 2011

Related U.S. Application Data

(60) Provisional application No. 60/885,030, filed on Jan. 16, 2007.

(51) Int. Cl.
*H01J 49/00* (2006.01)
(52) U.S. Cl. .................. 250/288; 250/281; 250/282
(58) Field of Classification Search .............. 250/281, 250/282, 288; 436/173; 128/200.23
See application file for complete search history.

(56) References Cited

U.S. PATENT DOCUMENTS

| 5,201,308 | A * | 4/1993 | Newhouse | 128/203.15 |
| 2004/0031486 | A1 * | 2/2004 | Schwarze et al. | 128/200.23 |
| 2004/0079881 | A1 * | 4/2004 | Fischer et al. | 250/288 |
| 2005/0035285 | A1 * | 2/2005 | Tan et al. | 250/288 |
| 2006/0225733 | A1 * | 10/2006 | Malhotra et al. | 128/200.23 |

FOREIGN PATENT DOCUMENTS

| EP | 1507282 | 2/2005 |
| WO | WP99/45362 | 9/1999 |

OTHER PUBLICATIONS

Canagaratna et al, "Chemical and microphysical characterization of ambient aerosols with the aerodyne aerosol mass spectrometer" Mass Spectrometry Reviews. 2007 (26) 185-222.
Gupta et al, "On-line high-performance liquid chromatography method for analyte quantitation from pressurized metered dose inhalers" J. Chromatogr A. 2004 (1033) 101-106.
Noble et al, "Single Particle Characterization of Albuterol Metered Dose Inhaler Aerosol in Near Real-Time" Aerosol Science and Technology. 1998 (29) 294-306.
International Preliminary Report on Patentability, Written Opinion of the International Searching Authority for Application No. PCT/SE2008/000027, dated May 12, 2008, 7 pages.
International Search Report for Application No. PCT/SE2008/000027, dated May 12, 2008, 4 pages.

* cited by examiner

*Primary Examiner* — Michael Maskell
(74) *Attorney, Agent, or Firm* — Finnegan, Henderson, Farabow, Garrett & Dunner, LLP (57) ABSTRACT

One aspect of the invention features a method of analyzing dose metered devices by: spraying an aerosol from a metered dose device directly into a spray chamber of a mass spectrometer detector by firing a dose from a metered dose device, for example a pMDI, by depressing the pMDI in its actuator, which spraying step is optionally preceded by a step of priming the drug container of the metered dose device; ionizing the aerosol; and identifying and quantifying the content of the dose using the detector.

21 Claims, 12 Drawing Sheets

METHOD AND SYSTEM FOR ANALYSING A DOSE FORMULATION OF A METERED DOSE DEVICE

TECHNICAL FIELD

The invention relates to analyzing a dose formulation of a metered dose device, e.g., a pMDI (pressurized Metered Dose Inhaler) dose formulation, and in particular, to the rapid analysis of a pMDI formulation that does not require any sample preparation before the analysis.

BACKGROUND

The common practice for analyzing dose contents of pMDIs is to tire a dose in the can through the actuator into a collection vessel. The dose is then washed down into a measuring, device and chemically analyzed, typically by a high performance liquid chromatograph (HPLC). When analyzing the dose content of other metered dose devices, such as a DPI (Dry Powder Inhaler) or a nasal spray, the preparation procedure is performed in a similar way. The preparation time when testing a single dose or a large number of doses is long for all the metered dose devices.

In addition, the analysis of leachables and excipients requires a in preparation process. Such a multi-step process for analyzing individual components of a drug dose is time-consuming.

The preparation and analysis time for such processes would be very costly for a large number of doses to be analyzed, which is often the case in the pharmaceutical industry. Thus, any process that reduces the required time of analysis and provides similar accuracy as conventional processes would be of significant value to the industry.

SUMMARY

The present invention provides a novel and efficient method of analyzing a dose formulation of a metered dose device, in particular a pMDI dose formulation, and an analysis system for performing the method.

In one aspect, the present invention features a method for the rapid analysis of a dose formulation of a metered dose device that does not require any sample preparation before the analysis, and which gives accurate results. This is accomplished by: spraying an aerosol from a metered dose device directly into a spray chamber of a mass spectrometer detector, by firing a dose from a metered dose device by activating it as a patient would, which spraying step is optionally preceded by a step of priming the drug container of the metered dose device; ionizing the aerosol; and identifying and quantifying the content of the dose using the detector.

This approach optionally includes a step of forming an aerosol. This step will be required for the DPTs and other metered dose devices comprising an aerosolizable powder material with a particle size equivalent to that of DPIs. In the case of small volume nebulizers, they can be used with or without the step of forming an aerosol. This approach may also involve the analysis of one or more doses. These may be introduced successively and analyzed individually.

In a second aspect, the invention features an analysis system for performing the above-mentioned analysis method. In one embodiment, the system includes a spectrometer, preferably a mass spectrometer, and a connecting means for fastening a metered dose device to the spray chamber of the mass spectrometer's detector. When mounted in the mass spectrometer, a dose in the form of an aerosol may be tired from the metered dose device, for example by depressing a pMDI in its actuator (as a patient would), directly into the detector spray chamber. In the spray chamber, the aerosol is ionized in such a way that the detector may identify and quantify its content.

The dose is sprayed directly into the analyzing equipment, in particular for a pMDI and nasal spray, eliminating any preparation of the dose formulation, such as dilution, and therefore reducing the use and subsequent need for disposal of solvent waste.

The lack of preparation of the dose material enables a very rapid and cost-effective method of analyzing the components of one dose of a metered dose device formulation (providing the dose content is ionizable by mass spectrometry).

Since the analyzed dose is fired through the actuator of a pMDI (or as nasal spray) in a very similar way a patient would use the pMDI, the analysis analyzes the dose content of a dose as the patient would experience it, i.e. the analysis gives a very realistic image of the actual dose content inhaled by the patient, which of course is a particularly important feature when dealing with the evaluation of pharmaceutical drugs and medical treatments.

With this approach, it is possible to identify and quantify, in addition to pharmaceutically active agents, a) excipients and b) leachable species contained in the pMDI, the actuator and contaminants from any secondary packaging material that could have been in contact with the pMDI (volatile species from the packing material could be present in the formulation). Analysis of leachables and excipients normally requires a multi-step preparation process, and would therefore greatly benefit from the rapid analysis method according to the present invention.

In addition, the analysis method according to the present invention may also function as a very rapid screening technique for the effect of material drug interactions. The rapid Screening works by adding additional material to the metered dose device and then assessing the actuation by looking for possible reactions/interactions. These could include degradation, addition and or sorption. Any species that can be ionized can be analyzed.

The analysis method according to the present invention is also able to detect contaminants in and/or degradents from the dose formulation.

The analysis method may also distinguish analyzed species based on an approximate particle size. The analysis will not generate a mass detection signal above a certain particle size, i.e. when obtaining an analysis result, the particles will automatically be below a certain size. If the particle size of the analyzed dose becomes too large, the signal/response from the detector will go to zero. This will depend on the mass spectrometer, but easily covers the range of particles of any common metered dose device and larger particles. This size may be determined by injecting particles having a fixed size and check when the signal is no longer obtained.

In the description above and below, the term "inhaler" is used frequently. This term includes various inhalers such as pMDIs, small volume nebulizers and DPIs, but also nasal sprays, or any metered dose device producing an aerosol or an aerosolizable powder material with a particle size equivalent to that of DPIs, which technically speaking may not be inhaled but which may be analyzed using the method and system according to the present invention.

DESCRIPTION OF DRAWINGS

FIGS. 3 & 4 show the result of the rapid analysis method when analyzing the content of commercially available pMDIs and their main component.

DETAILED DESCRIPTION

In one embodiment of the analysis method, the method comprises the steps of:
mounting a pMDI and actuator into a spray chamber of a mass spectrometer detector using a connection means, such that a dose of the pMDI may be fired directly into the detector spray chamber;
spraying an aerosol directly into the chamber by firing a dose from the pMDI by depressing the pMDI in its actuator;
ionizing the aerosol;
identifying and quantifying the content of the dose using the detector.

In another embodiment, the method comprises the steps of;
mounting a nasal spray into a spray chamber of a mass spectrometer detector using a connection means;
spraying an aerosol spray directly into the chamber by firing a dose from the nasal spray by manipulating its actuator;
ionizing the aerosol spray;
identifying and quantifying the content of the dose using the detector.

In still another embodiment, the method comprises the steps of:
mounting a DPI into a spray chamber of a mass spectrometer detector using a connection means;
manipulating the actuator of the DPI in order to dispense a dose;
sucking the dry powder of the DPI into the spray chamber by applying a sufficient underpressure in the detection chamber, or blowing or pushing the dry powder into the device by applying a sufficient pressure, to convert the dry powder into an aerosol;
ionizing the aerosol;
identifying and quantifying the content of the dose using the detector.

The mounting step may include fastening the metered dose device, using the connection means, in an air-tight fashion in order to avoid loss of material.

The spraying step is preferably preceded by a step of priming the drug can or container of the pMDI or the nasal spray. For pMDIs, the priming step is normally performed when not mounted in the MS, since the accuracy of the injection will be better if the device is shaken before priming and injection of the dose into the MS. This procedure also mimics the way a patient would use the device. In the case of DPIs, the priming step may not be necessary to obtain accurate results, but when a blowing action is employed to move the powder from the inhaler to the spray chamber, then the priming step is preferably performed when not mounted in the MS.

The step of sucking the dry powder into the detector spray chamber may be replaced with a step of blowing the dry powder into the spray chamber. However, the suction procedure is preferred since it better resembles the inhalation procedure performed by a patient. The suction force may be applied in a constant fashion, but may also be coordinated with the injection of the aerosol. The suction force may also exhibit a specific suction force profile, so that the drug dose will be sucked into the spray chamber in a manner resembling the patient's inhalation of the drug. The suction force may be applied in a constant fashion, but may also be coordinated with the injection of the aerosol. The suction force may also exhibit a specific suction force profile, so that the drug dose will be sucked into the spray chamber in a manner resembling the patient's inhalation of the drug.

The method of analysis may also involve the analysis of other materials than those mentioned above, with the proviso that the material has a small particle size and may be aerosolised. The correct particle size is easily determined by the presence of a detection signal in the MS or not as discussed above in connection with the detectable particle size.

The metered dose devices may be selected from pressurized metered dose inhalers (pMDIs), Dry Powder Inhaler (DPIs), nasal sprays, small volume nebulizers, and any metered dose device producing an aerosol or a powder material with a particle size equivalent to that of DPIs.

The method of analysis may also include the analysis of the content of more than one dose at the same time. This is simply performed by introducing several successive doses into the detector spray chamber and analyzing all of them individually. The procedure may in some cases require priming of the drug container before each spraying.

In the following description of conventional MS systems or the analysis system according to the present invention, the same reference numbers have been used for the same elements.

Figure 11:
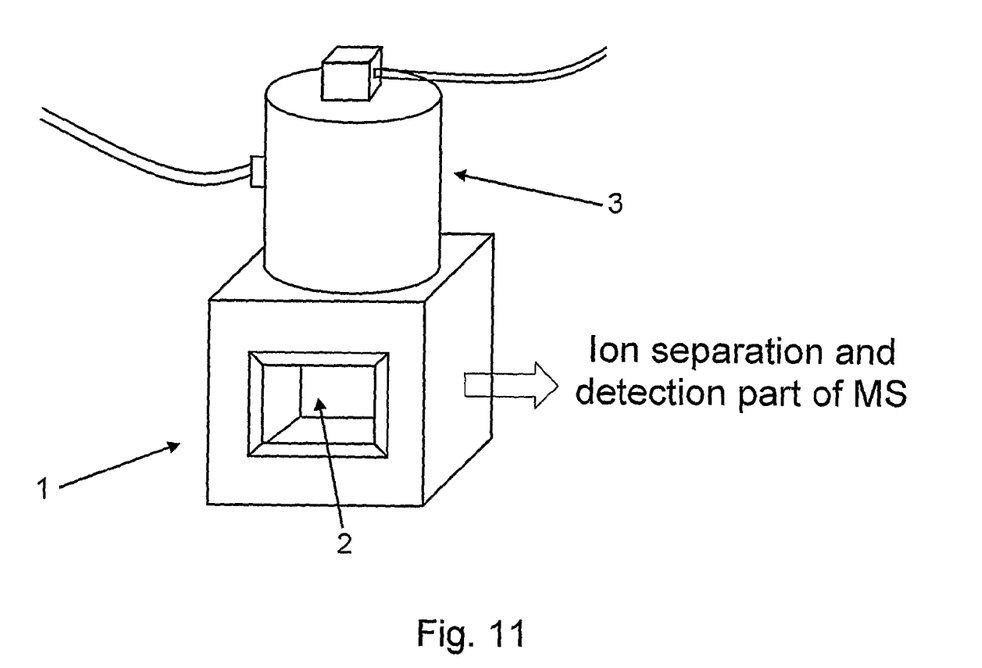
FIG. 11 is a perspective view from the frontside of a conventional MS analysis system, where the spray chamber of the detector is open.
Figure 12:
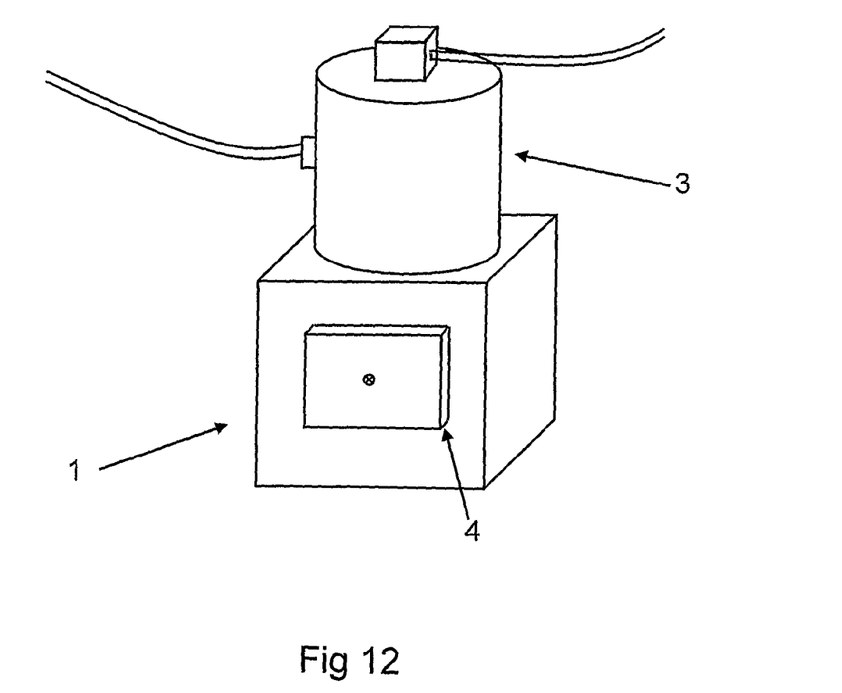
FIG. 12 is a perspective view from the frontside of a conventional MS analysis system, where the spray chamber of the detector is closed.

FIG. 11 shows an example of a conventional MS analysis system (1), including a detector spray chamber 2 (the spray chamber being, composed of the ionizer (not shown) and a detector 3). The figure depicts the system when the spray chamber is open. FIG. 12 shows the same system when the spray chamber has been sealed by a lid 4 fastened by fastening elements.

The analysis system basically comprises the same components as the conventional MS systems, the difference being that access to the spray chamber has been created, enabling injection from a metered dose device directly into the spray chamber.

Figure 13:
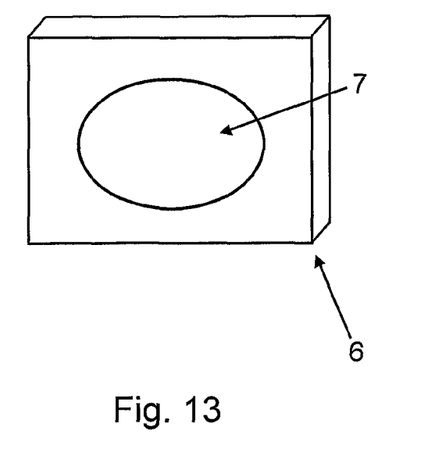
FIG. 13 is a perspective view from the frontside of the connecting means used in the analysis system.

FIG. 13 shows an embodiment of a connecting means 6 used in the analysis system. The connecting means is adapted to receive a metered dose device 8. The connecting means is normally provided with an opening. When preparing for the direct injection, the metered dose device is inserted into the opening 7 in the connecting means, such that the outlet of the metered dose device is facing the inside of the detector spray chamber, and enables actuation of a drug from the metered dose device directly into the spray chamber. The opening 7 may optionally be provided with some sealant material in order to prevent blowback.

Figure 14A:
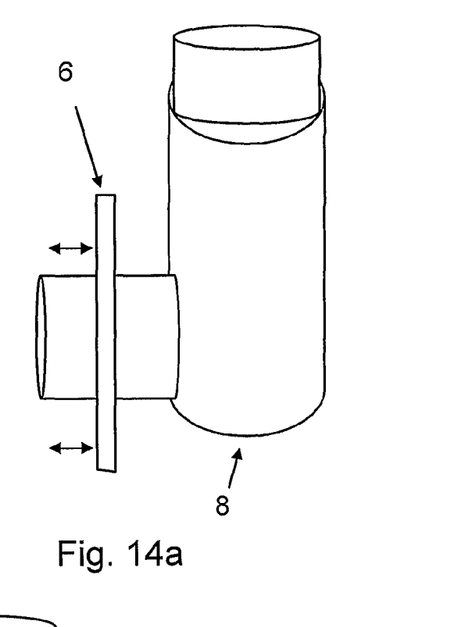
FIG. 14a is a perspective view from the side of an metered dose device inserted into the connecting means.
Figure 14B:
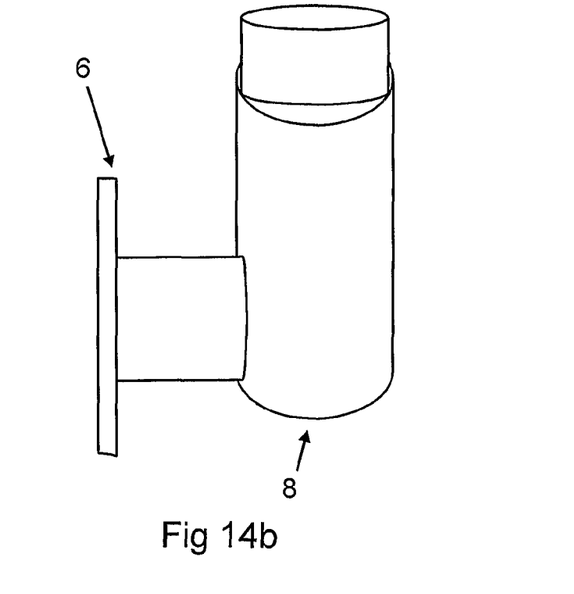
FIG. 14b is a perspective view from the side of metered dose device according to FIG. 14a, but where the metered dose device is in a position that is typical for use in the method and system.

FIG. 14a shows a sideview of a metered dose device 8 inserted in the connecting means 6. The double-headed arrows indicate that the positions of the metered dose device can be adjusted. In this embodiment, the metered dose device is represented by a pMDI inhaler. The connecting means, including the metered dose device is then fastened by conventional fastening means, such as a screw. In FIG. 14b is a perspective view from the metered dose device is in a position that is typical for use in the method and system according to the present invention.

Figure 15:
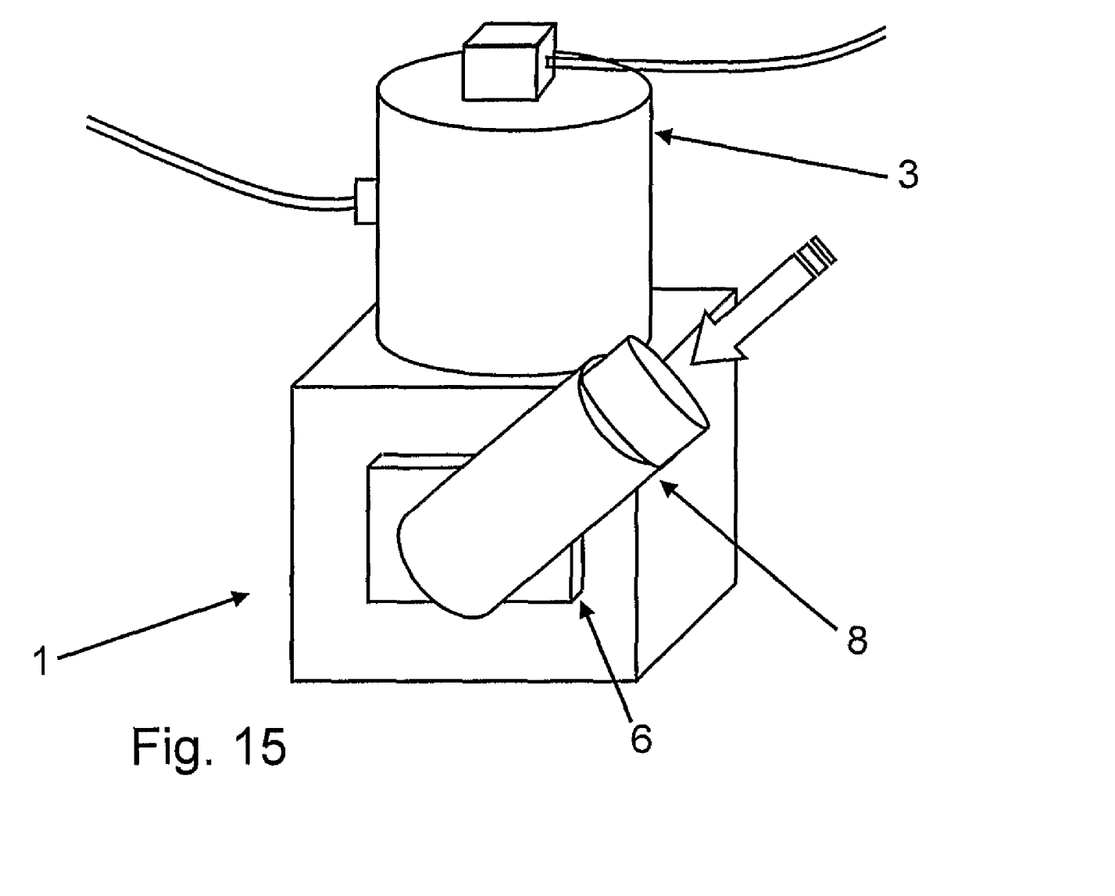
FIG. 15 is a perspective view from the frontside of the analysis system in operation.

FIG. 15 shows an analysis system according to the present invention when in use. The connection means/metered dose device ensemble is mounted in the analysis system. During operation, the operator depresses the drug can or container of the pDMI into its actuator. This is indicated by an arrow. The drug dose is then injected directly into the detector spray chamber.

In one embodiment of the analysis system for performing the above-mentioned method, the system comprises a mass spectrometer, a connecting means for fastening a metered dose device to the spray chamber of the mass spectrometer detector, and a means of ionizing any aerosol sprayed into the spray chamber such that the detector may identify and quantify the components of the aerosol. The system may optionally comprise a suction means, for sucking any powder material into the spray chamber and producing an aerosol that is ionizable. Instead of a suction means, the system may optionally comprise a blowing means, for blowing any powder material into the chamber. If the inhaler comprises a propellant, the propellant is used to propel the material into the mass spectrometer.

When mounted in the mass spectrometer, a dose in the form of an aerosol may be fired by manipulating the device (for example by depressing the drug can/container in its actuator in the case of a pMDI), from the metered dose device directly into the detector spray chamber. In the spray chamber, the aerosol is ionized, and its content is identified and quantified by the detector.

The system may also comprise an aerosolisation means for converting material of small particle size into an ionizable aerosol. In standard MS system, such an aerolisation means is included.

Normally, the detector spray chamber of a mass spectrometer is covered by a protective plate in the form of a metal plate. Such a metal plate normally features a viewing glass, through which the analysis procedure may be monitored. Note if a viewing window is not available then a suitable hole would need to be made into the spray chamber.

As stated in the Summary, the analysis method according to the present invention may be performed without any aids, by simply spraying a dose into the spray chamber of the detector of a mass spectrometer. However, this could lead to significant aerosol plume losses due to blowback. In more preferred embodiments, a number of additions have been used to aid the firing of the metered dose device into the spray chamber.

One way of avoiding blowbacks is to arrange the metered dose device and actuator in the mass spectrometer by a connecting means. According to the present invention, the protective plate of a conventional mass spectrometer may be replaced by a connecting means as disclosed in the present application. Such a connecting means may have different shapes, but could for example be a square-formed metal plate adapted to secure the actuator of an inhaler to the spray chamber of a detector, i.e. a metal plate into which the actuator of the pMDI has been inserted. The connecting means may have any shape as long as it is suitable for the purposes of the present invention. The material of the connecting means may also vary, but a metal is normally preferred due to properties such as inertness and ease of manufacture. The connection is preferably an air-tight arrangement preventing any material from escaping the detector spray chamber. Conventional inert sealing materials may be used to ascertain an air-tight fastening of the inhaler in the MS. However, a completely air-tight mounting of for example a pMDI is not possible, since normally a pMDI and its actuator comprises airways. The connecting means is made of a material with high temperature stability, i.e. able to withstand the to high temperatures of the ordinary use of the MS instrument.

Figure 8:
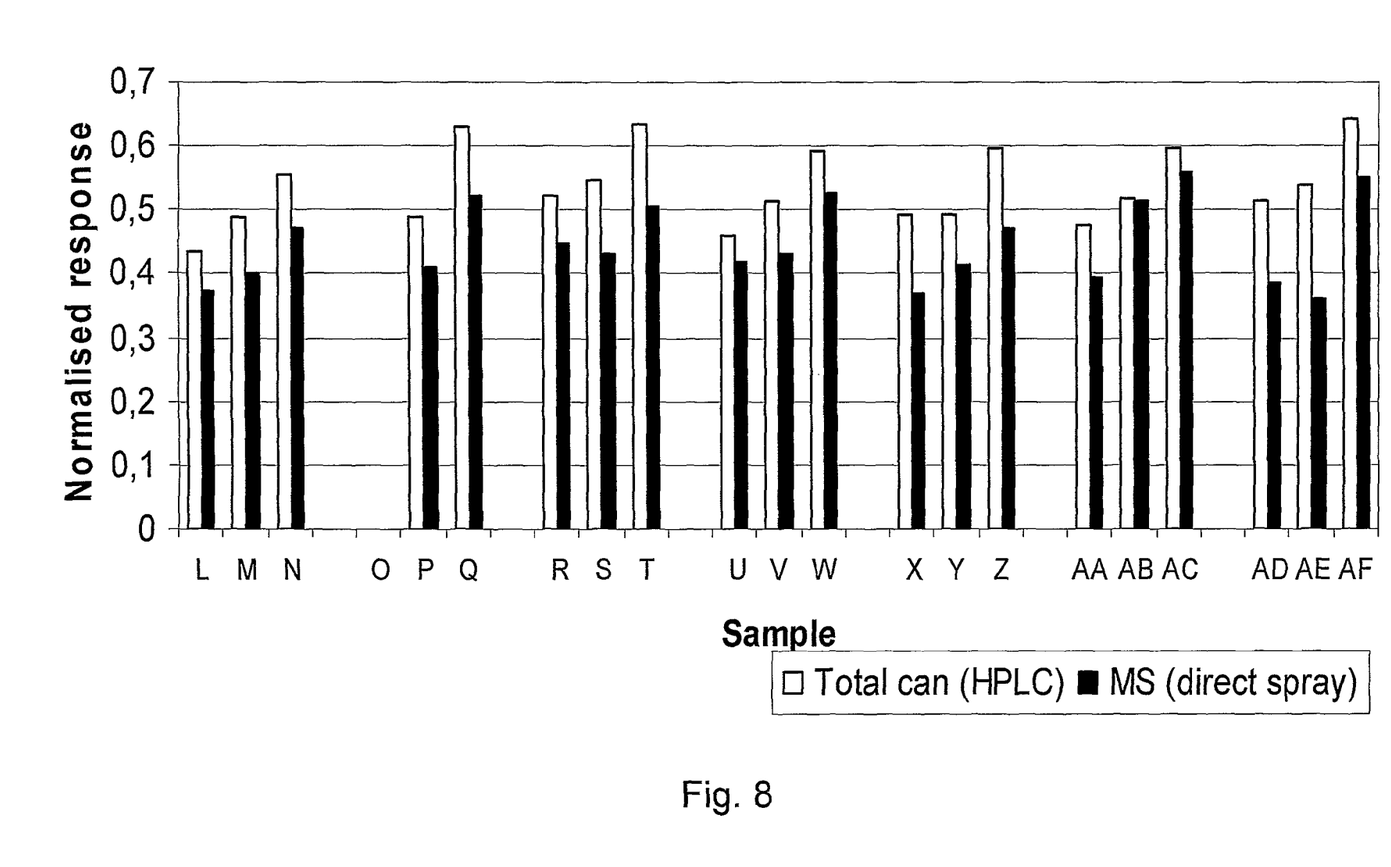
FIG. 8 is a comparison between standard analysis technique and the direct spray method according to the present invention.

When comparing the standard techniques and the direct spray technique, it is noted that the direct spray technique has a lower response because no washing step is involved which increases the amount of the species in solution. This leads to a lower response signal. As seen in FIG. 8, the direct spray technique provides a sufficiently is good analysis result.

After priming the pMDI, the protective plate is removed from the detector spray chamber and replaced with the metal plate fitted with the pMDI/actuator, the pMDI is then actuated in the normal way.

Additional liquids may also be added to the mass spectrometer detector spray chamber when performing the direct injection. The liquid may be injected into the detector 3 in a way as used when performing conventional MS using a conventional MS device. A liquid could be added, as depicted in for example FIG. 15, via the tubing, through the box (on top of the detector), and into the detector 3. The liquid sample may be added to aid ionization. An ionization aid may typically be a proton donating solvent, such as methanol. External addition of ionization aids or other liquids that may enhance the analysis results also keeps the detector spray chamber cleaner. The choice of solvent and flow conditions will affect the response, but these will be optimized depending on the species tested. If no solvent is used, the process still works but not as effectively.

Parameters for the LC-MS (liquid chromatography mass spectroscopy) system according to the present invention have been optimized to maximise the response to the various species present in the pMDI, Various modes of ionization, such as APCI (Atmospheric Pressure Chemical Ionization), EST (Electrospray Ionization), APPI (Atmospheric Pressure Photo ionization) have been investigated. APCI and APPI have been found to be the preferred modes of ionization since they yield the best and most consistent response, with APCI generally being used most frequently. The ionization mode may be optimized for different species. Different spray solvents may be required, possibly also with dopants. APPI typically uses a dopant to allow a charge transfer ionization to enable ionization. Dopants can optionally be used when the ionization method is selected from for example ESI or APCI.

EXAMPLES

Example 1

Figure 1:
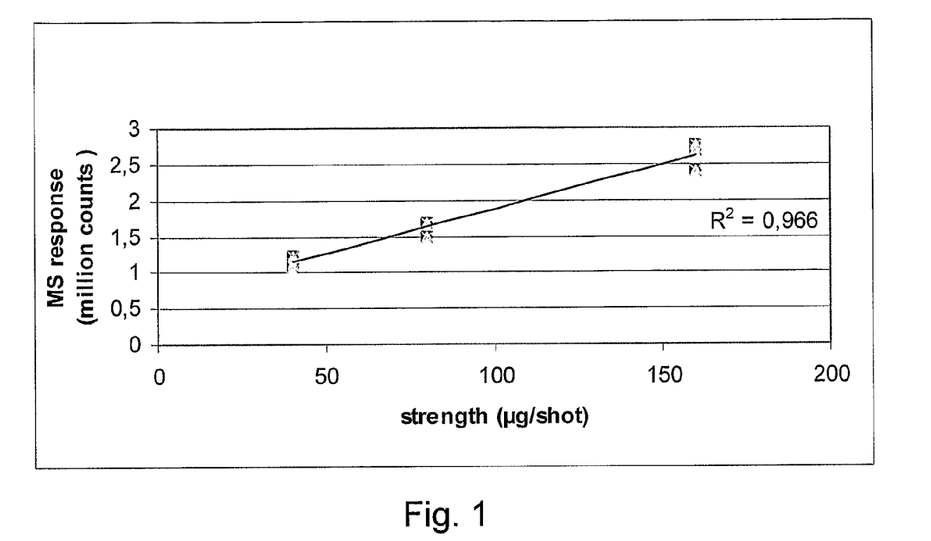
FIG. 1 is a dose linearity plot showing the result of the rapid analysis method.

In Example 1 a pMDI (comprising Budesonide and Formoterol as active agents) was mounted in the system according to the present invention, and activated directly into the detector spray chamber of the MS. The ionization method used was APCI. The is result of the injections performed with varying dose strength (of Budesonide) is presented as FIG. 1. The graph shows that the active agent could be detected and that the detection was reproducible and a linear response was obtained.

Example 2

Figure 2:
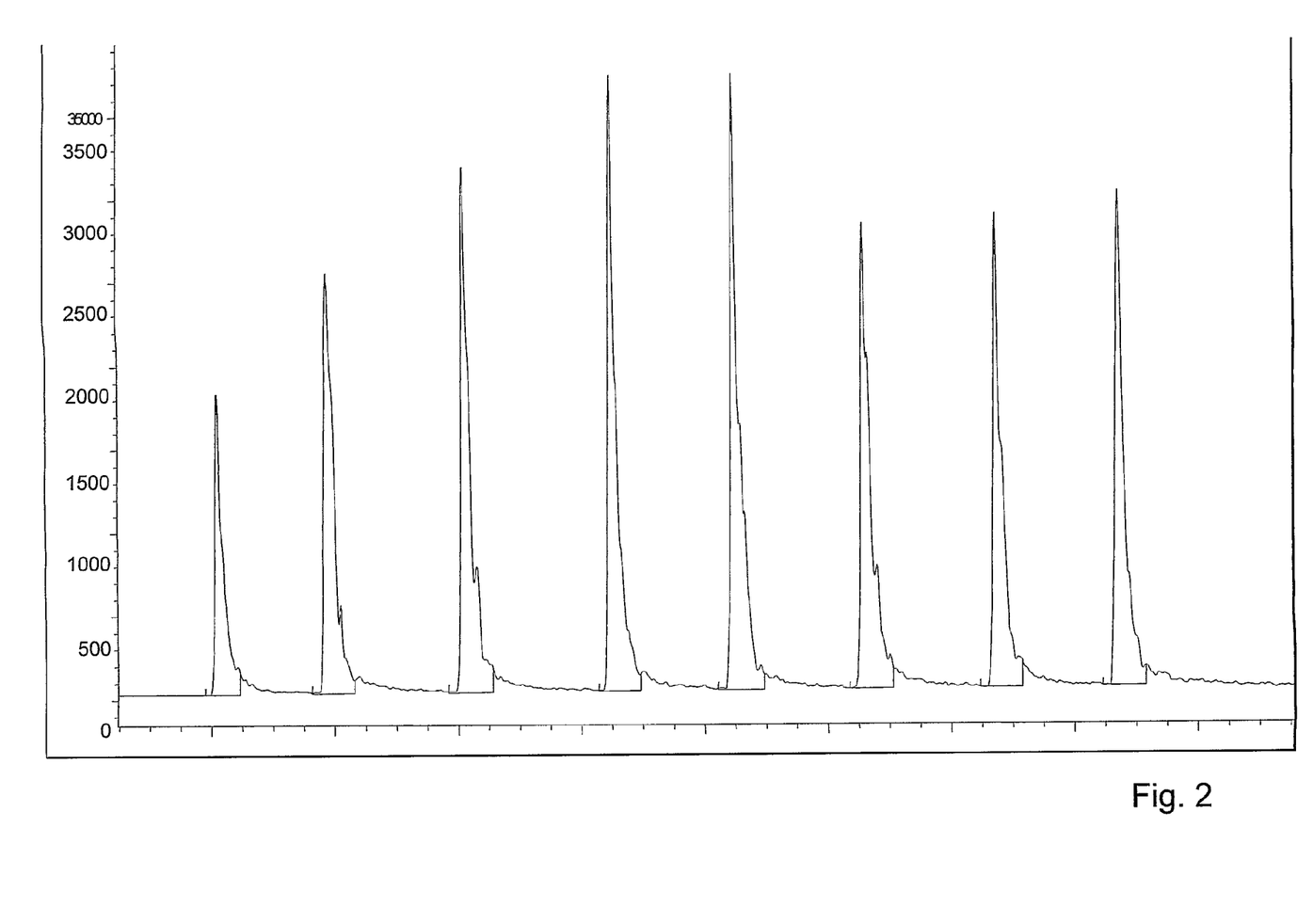
FIG. 2 shows the applicability when using Atmospheric Pressure Photo Ionization (APPI).

In FIG. 2, the applicability of the direct analysis method (also testing a pMDI) according to the invention when using APPI ionization is shown. The experiment was performed by direct injection using varying dose strength (of Budesonide). The graph shows the total ion current of each injection (total detected mass). The graph shows only shows the responses for one of the dose strength's used. The y-axis represents counts and the x-axis time in minutes.

Example 3

Figure 3:
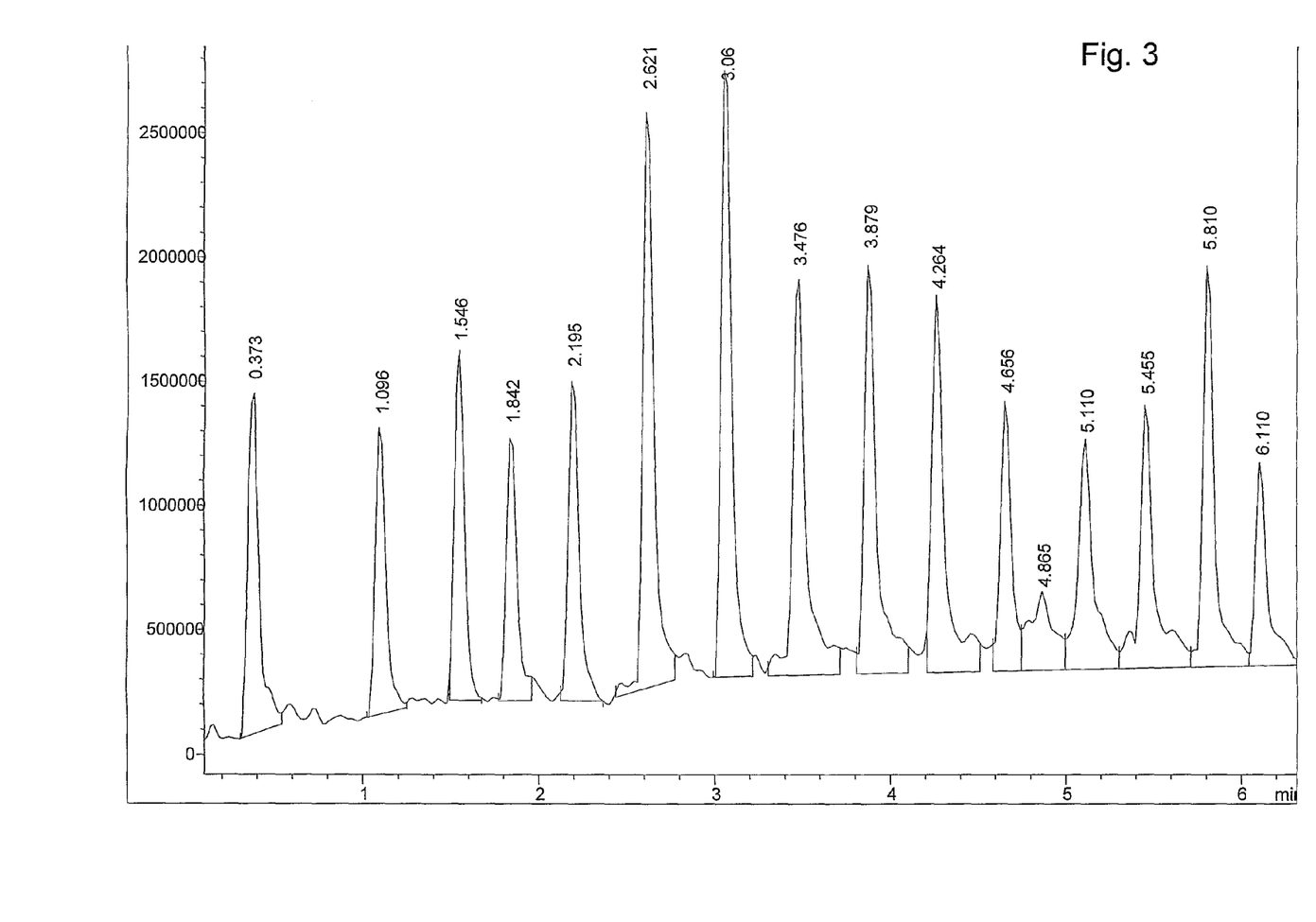
FIG. 3 is the total ion chromatogram.
Figure 4:
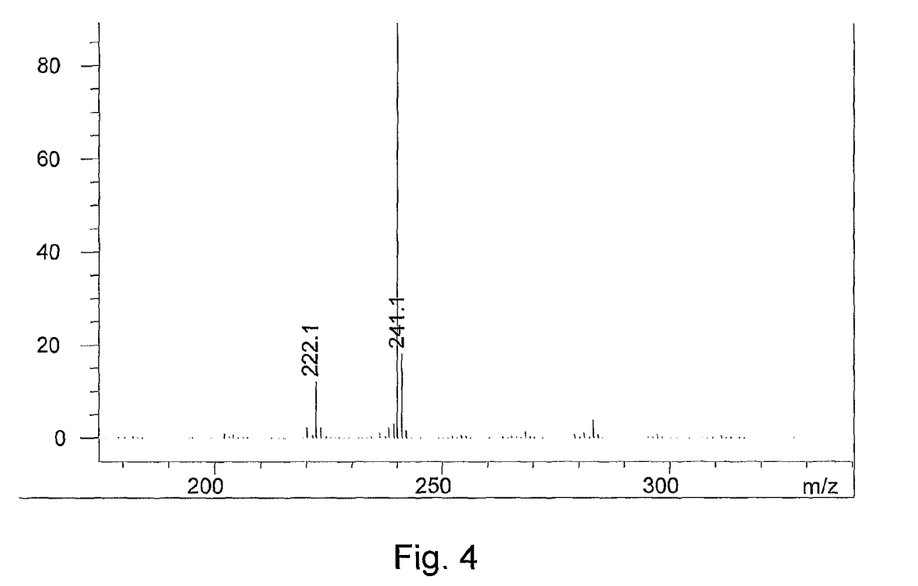
FIG. 4 shows the mass spectrum of the main component.

FIGS. 3 and 4 show the result of the rapid analysis procedure when analyzing the content of commercially available pMDIs and their main component. The following pMDIs were used: Proventil (active agent: albuterol sulfate), Qvar (active agent: HFA beclomethasone dipropionate and Ventolin (active agent: salbutamol). The responses were not optimized, but identification of the main components were possible in all three cases).

FIG. 3 shows the total ion current detected. 5 shots were injected for each pMDI, representing the peaks 1-5, 6-10, and 11-15 in the figure. The y-axis represents counts and the x-axis time in minutes. FIG. 4 shows the mass spectrum of the main component of one of the pMDIs. The y-axis represents the relative intensity.

Example 4

Figure 5:
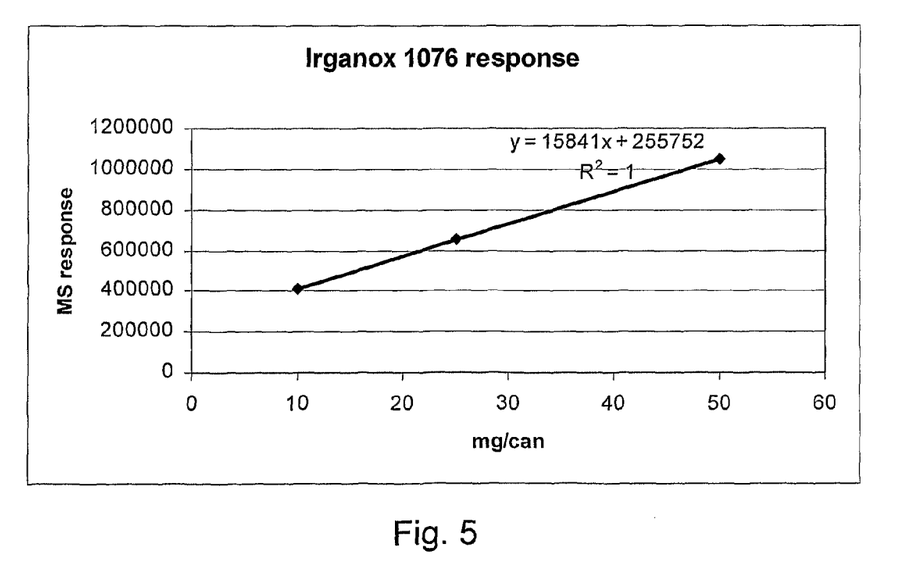
FIG. 5 is a linearity plot of a spiked leachable species.

In order to test if the method according to the present invention could be used for in detecting leachable substances. i.e. emanating from for example the package material or inhaler construction material, tests were performed with Irganox 1076, a commercial antioxidant found in the actuator and valve in pMDIs. FIG. 5 is a linearity plot showing the result of direct spray of spiked pMDIs using fixed concentrations of the leachable species. The graph shows that the leachable species could be detected and that the is detection was reproducible. In this example, the ionization method was APCI.

Example 5

Figure 6:
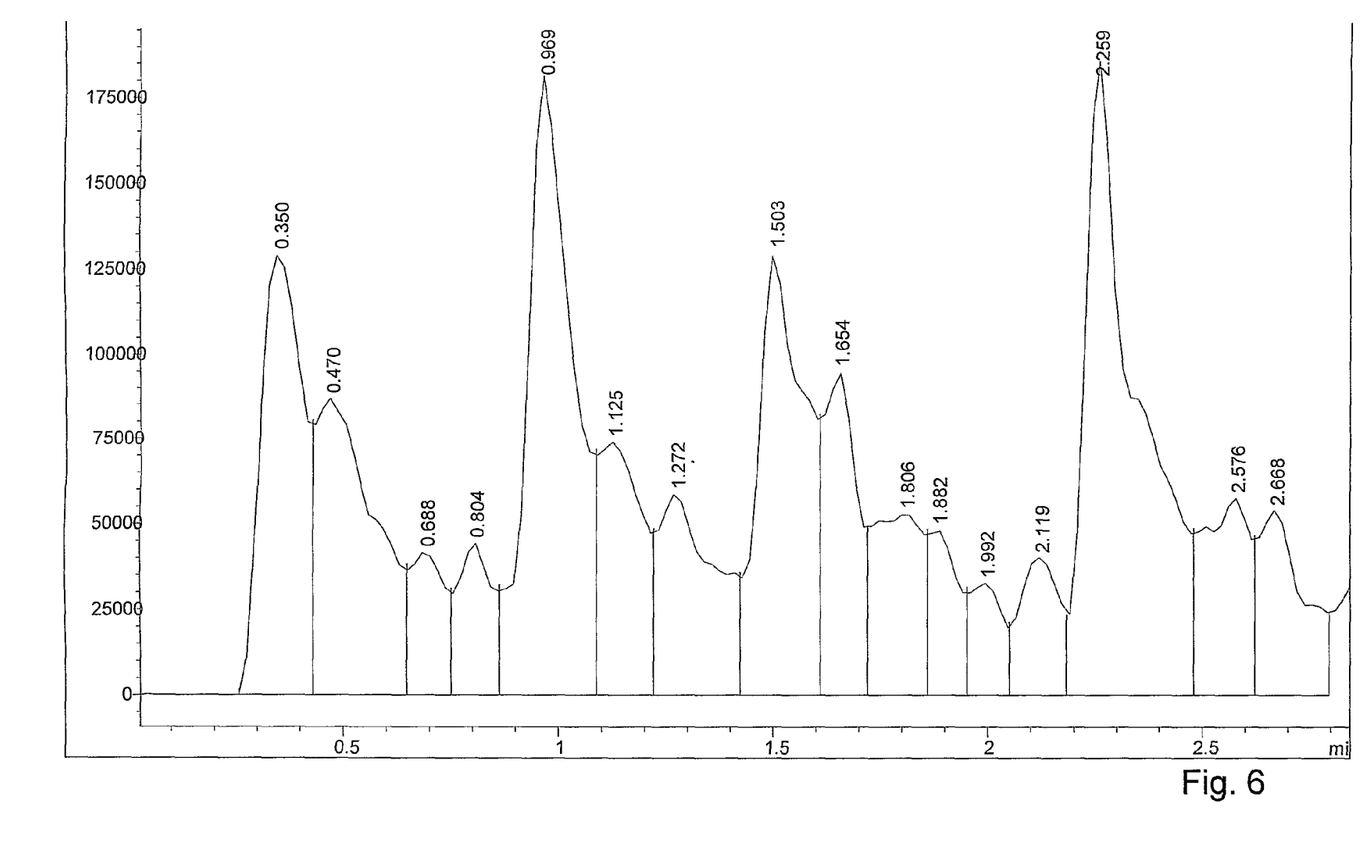
FIG. 6 is the total ion chromatogram for excipients.
Figure 7:
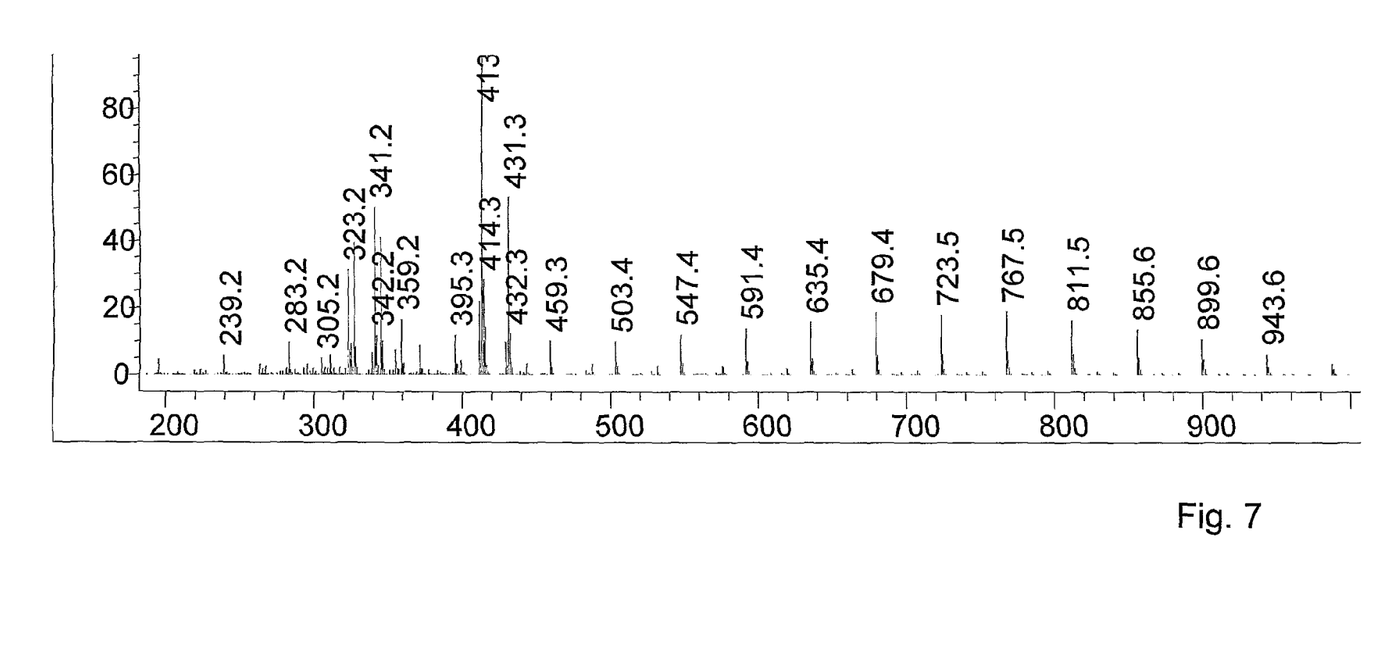
FIG. 7 is a mass spectrum of the pMDI contents.

In order to test if the method according to the present invention could be used for detecting excipients/degradents, tests were performed with a pMDI comprising PEG (Polyethylene glycol) (PEG is a common excipient). FIG. 6 the total response to a single PEG isomer when only the ion pertinent to the PEG isomer is selected. The y-axis represents counts and the x-axis time in minutes.

Example 6

In this experiment, a standard wet chemistry analysis technique, in this case HPLC, was compared with the direct spray analysis according to the present invention. This experiment was performed to investigate the effect of rubber (used for parts in the inhaler) on the effective dose of an active agent. Letters L-Z and AA-AF in FIG. 8 represent the tests performed was with the same different strength of an active agent and varying rubber materials. The rubbers were also subjected to different treatments.

Example 7

Figure 9:
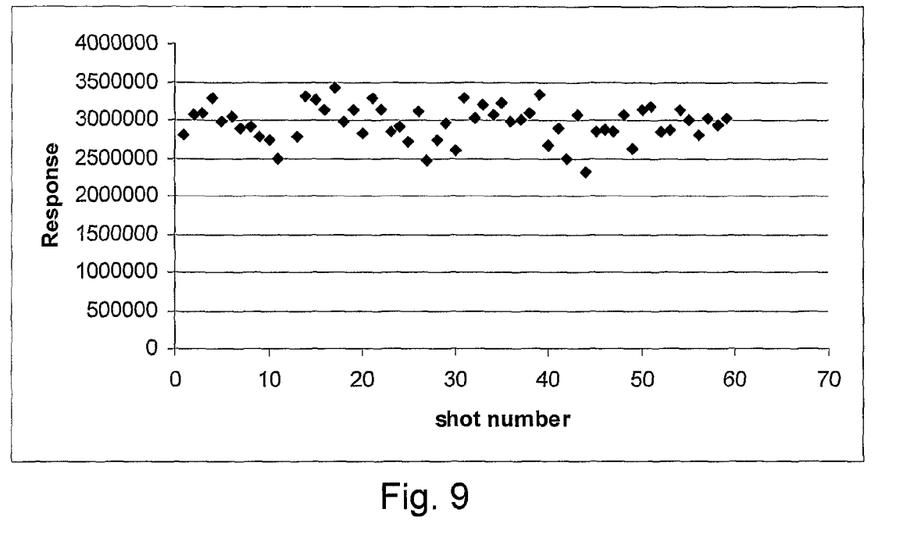
FIG. 9 is a dot plot showing the reproducibility of the analysis method.

The reproducibility of the method according to the present invention was tested by injecting all the does from an inhaler can (test of through can life). FIG. 9 is a dot plot Showing the reproducibility of the method.

Example 8

The analysis method and system according to the present invention were also used to study chemical interactions. By performing various direct injections using different active agents, additives, component materials in the inhalers, etc., and comparing the mass spectrograms from these tests with reference chromatograms with controlled presence of the analyzed substances, reactions/interactions between the substances could be detected. These reactions included degradation, addition and or sorption reactions. In addition, contaminants and reaction with contaminants could be detected. The present direct spray procedure thus enables a rapid teal-tune monitoring tool for the production of metered dose devices and their constituents.

Example 9

Figure 10:
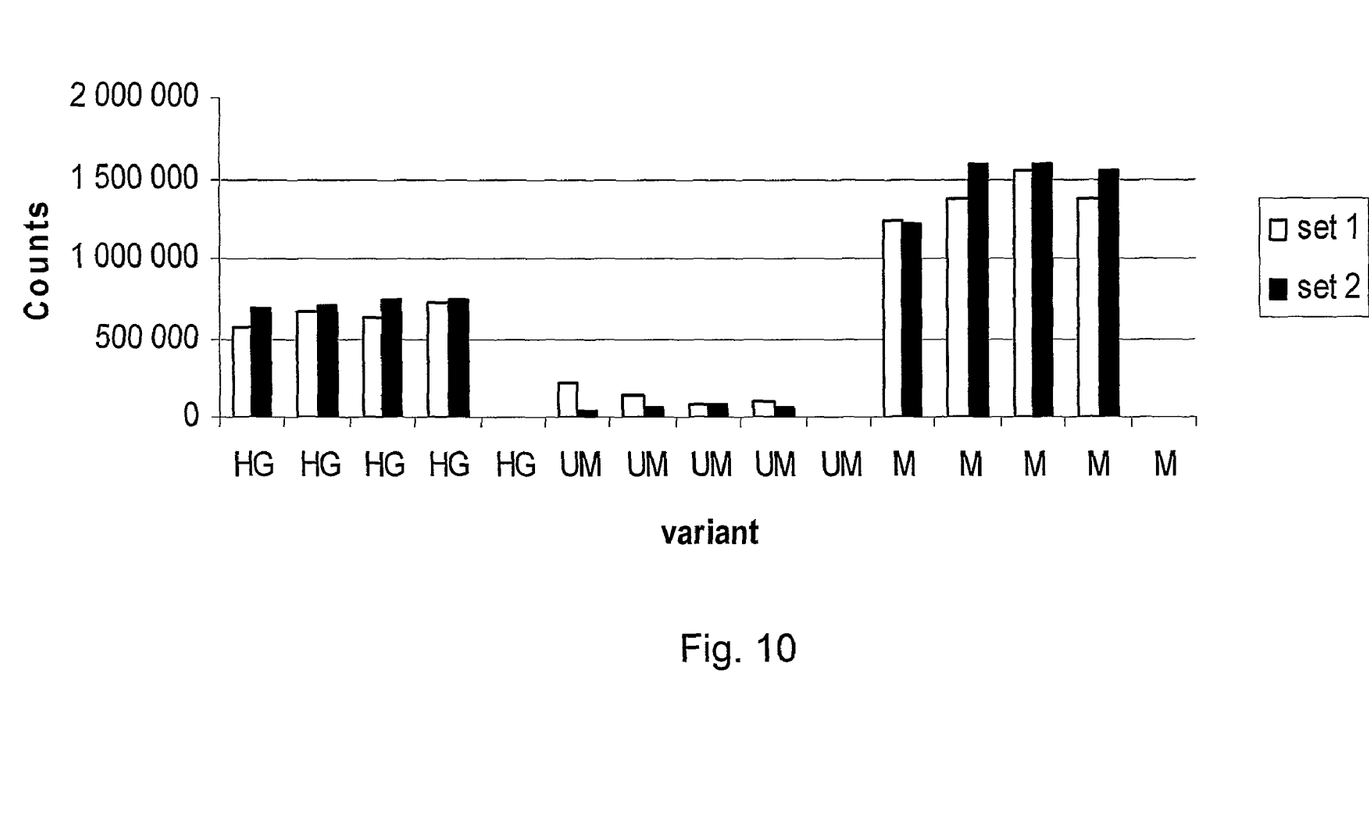
FIG. 10 shows impact of particle size on the response signal when using the direct spray method.

In this experiment, the analysis method and system according to the present invention were used for assessing the crude particle size of the material in the dose formulation or aerosol. FIG. 10 shows the response signals for particles of an active agent (Budesonide) that had been ground by hand (HG), unmicronised particles (UM) and micronised (M).

What is claimed is:

1. A method of analyzing metered dose devices, the method comprising:
    spraying an aerosol from a metered dose device directly into a spray chamber of a mass spectrometer detector by activating a patient-actuatable spray actuator of the metered dose device to fire a metered dose of the aerosol from the metered dose device into the spray chamber;
    ionizing the metered dose of the aerosol in the spray chamber; and
    at least one of identifying and quantifying the metered dose content contained within the spray chamber with the mass spectrometer detector.

2. The method of claim 1, further comprising priming a drug container of the metered dose device prior to spraying the metered dose of the aerosol from the metered dose device directly into the spray chamber.

3. The method of claim 1, wherein spraying the metered dose of the aerosol from the metered dose device directly into the spray chamber of the detector comprises spraying several successive doses into the spray chamber of the detector, and wherein the at least one of identifying and quantifying the metered dose content contained within the spray chamber with the detector comprises at least one of identifying and quantifying the metered dose content of each successive metered dose individually.

4. The method of claim 1, further comprising removably fastening the metered dose device onto the spray chamber using a connector into which the metered dose device is inserted.

5. The method of claim 1, wherein ionization of the aerosol is performed by using at least one of Atmospheric Pressure Chemical Ionization, Atmospheric Pressure Photo Ionization, and Electrospray Ionization.

6. A dose analysis system comprising:
 a connector configured to removably fasten a metered dose device to a mass spectrometer to fluidly connect the metered dose device to a spray chamber of the mass spectrometer such that an outlet of the metered dose device is directed into the spray chamber and the metered dose device is accessible to allow actuation of the metered dose device to spray a drug directly into the spray chamber.

7. The method of claim 1, further comprising producing the metered dose of the aerosol from a powder material prior to spraying the metered dose of the aerosol directly into the spray chamber.

8. The method of claim 7, wherein producing the metered dose of the aerosol from the powder material is performed by at least one of sucking, blowing and pushing the dry powder into the spray chamber by applying a pressure to the powder material with sufficient suction force to produce the metered dose of the aerosol.

9. The method of claim 1, wherein the metered dose content includes at least one of a pharmaceutically active agent, a leachable, a contaminant, an excipient, and a degradent from a dose formulation.

10. The method of claim 1, further comprising analyzing a particle size of at least one of a dose formulation and the metered dose of the aerosol based on the at least one of identification and quantification of the metered dose content.

11. The method of claim 1, further comprising analyzing the interactions between an active agent and at least one other component produced by the metered dose device based on the at least one of identification and quantification of the metered dose content.

12. The system of claim 6, wherein the metered dose device is selected from the group consisting of pressurized metered dose inhalers (pMDIs), small volume nebulizers, nasal sprays, and metered dose devices producing an aerosol.

13. The system of claim 6, wherein the connector includes a surface defining an opening configured to receive the outlet of the metered dose device.

14. The system of claim 13, wherein the opening is generally oval shaped.

15. The system of claim 6, wherein the connector is substantially planar.

16. The system of claim 6, further comprising a device configured to aerosolize a powder material of small particle size into an ionizable aerosol.

17. The system of claim 6, further comprising the mass spectrometer.

18. The system of claim 13, wherein the outlet of the metered dose device is slideably locatable within the opening to adjust the length of the outlet that extends through the opening.

19. A method of quantifying a dose produced by a metered dose device, comprising:
 fluidly coupling an outlet of the metered dose device to a spray chamber of a mass spectrometer;
 activating the metered dose device to produce a dose;
 delivering substantially all of the dose through the outlet and into the spray chamber;
 delivering a stream of ions to the spray chamber to ionize substantially all of the dose delivered to the spray chamber; and
 determining a quantity of substantially all of the dose based on measuring substantially all of the ionized dose in the spray chamber.

20. The method of claim 1, wherein ionizing the metered dose is performed prior to conducting any type of analysis of the metered dose.

21. The system of claim 16, wherein the metered dose device is selected from the group consisting of Dry Powder Inhalers (DPIs), small volume nebulizers, and metered dose devices comprising an aerosolizable powder material with a particle size equivalent to that of DPIs.

* * * * *